United States Patent [19]
Patrick, Jr.

[11] Patent Number: 4,538,612
[45] Date of Patent: Sep. 3, 1985

[54] SKIN PREPARATION METHOD AND PRODUCT

[75] Inventor: Charles T. Patrick, Jr., Dayton, Ohio

[73] Assignee: NDM Corporation, Dayton, Ohio

[21] Appl. No.: 527,095

[22] Filed: Aug. 29, 1983

[51] Int. Cl.³ .................. A61B 17/00; A61B 5/04
[52] U.S. Cl. .................................. 128/333; 128/639; 128/803; 15/159 A; 51/392; 51/400; 206/363
[58] Field of Search ............... 128/639-641, 128/643, 644, 798, 802, 803, 333, 355, 304; 433/125, 142, 166; 206/363, 367, 438; 132/76.4, 76.5; 51/391, 392, 393, 400; 30/164.9; 15/167 R, 159 A

[56] References Cited

U.S. PATENT DOCUMENTS

| | | | |
|---|---|---|---|
| 34,677 | 3/1862 | Firmenich | 128/333 |
| 583,098 | 5/1897 | Thomas | 15/111 |
| 1,268,343 | 6/1918 | Greenbowe | 30/164.9 |
| 2,712,823 | 7/1955 | Kurtin | 128/303 |
| 2,881,763 | 4/1959 | Robbins | 128/355 |
| 2,887,112 | 5/1959 | Smith | 128/644 |
| 3,447,181 | 6/1969 | Coker et al. | 206/363 X |
| 3,505,993 | 4/1970 | Lewes et al. | 128/643 |
| 3,613,143 | 10/1971 | Muhler et al. | 15/167 R |
| 3,774,592 | 11/1973 | Lahr | 128/640 |
| 3,911,906 | 10/1975 | Reinhold, Jr. | 128/641 |
| 4,004,578 | 1/1977 | Palmius | 128/640 |
| 4,274,419 | 6/1981 | Tam et al. | 128/639 |
| 4,311,152 | 1/1982 | Modes et al. | 128/641 |
| 4,462,136 | 7/1984 | Nakao et al. | 15/167 R |

OTHER PUBLICATIONS

Burbank et al., "Reducing Skin Potential ... Abrasion", Med. & Biol. Eng. & Comput., 1978, 16, 31-38.

*Primary Examiner*—Lee S. Cohen
*Attorney, Agent, or Firm*—Dybvig & Dybvig

[57] ABSTRACT

Epidermal tissue is prepared and marked prior to attachment thereto of an electrode, such as an electrocardiograph electrode, by gently stroking the epidermal surface with an abrader device having fibers adequately stiff to dislodge cells from the epidermal tissue. The abrader device is sterilized and stored in a protective container prior to use.

12 Claims, 4 Drawing Figures

SKIN PREPARATION METHOD AND PRODUCT

SUMMARY OF THE INVENTION

It has been a practice in the use of medical electrodes, whether for monitoring tissue conditions or treating tissue by means of electrical stimulation, to prepare the skin of a patient who is to receive any such monitoring or treatment by cleaning the skin as with alcohol and, thereafter, vigorously rubbing and thus abrading the skin, with such abrasion ordinarily producing an erythema. Such abrasion procedure is typically followed by an application of a saline solution or electrolyte to the skin so as to form a bridge between the prepared skin and an electrode, which bridge transmits signals between the prepared skin and the electrode. In accordance with the present invention, it has been discovered that instead of vigorous rubbing and consequent abrasion of the skin, a fully adequate preparation can be accomplished by stroking an abrader device containing a bundle of fibers rather gently along the skin of a patient where monitoring or treatment is to occur. This stroking, in addition to reducing the electrical impedance of the skin, also temporarily marks the skin by whitening it along the stroked lines, thus allowing the operator to readily identify portions of the skin that have been prepared for ensuing monitoring or treatment.

DETAILED DESCRIPTION

Figure 1:
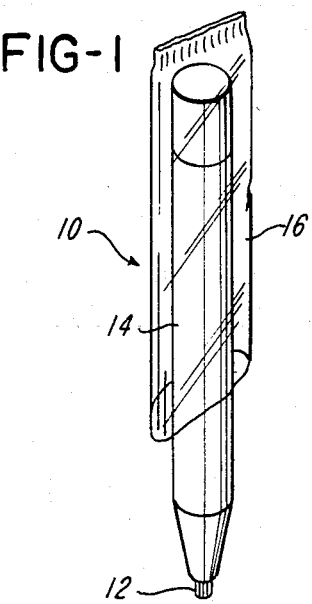
FIG. 1 is an isometric illustration of an abrader device in accordance with the present invention and a container therefor, the container having been broken open and partially removed from the abrader device.
Figure 2:
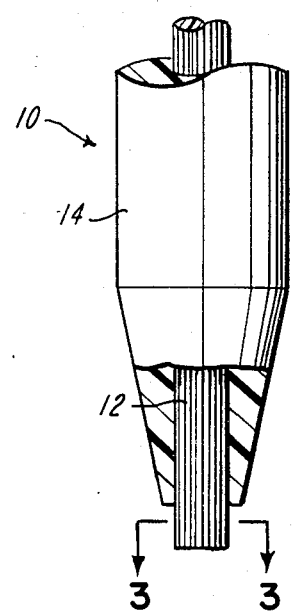
FIG. 2 is an enlarged illustration of the abrader device with its upper end broken away and with a portion of its lower end also broken away.
Figure 3:
FIG. 3 is a sectional illustration taken substantially along the line 3—3 of FIG. 2.

FIG. 1 is an isometric illustration showing a commercially available abrader device 10 of the type used by draftsmen in correcting inked drawings, the abrader device 10 comprising a relatively stiff bundle of densely packed fibers 12, such as glass fibers, gathered and retained within a housing 14 which may be, for example, a molded plastic housing. Mechanism (not shown) may be incorporated within the housing to extend and withdraw the bundle from and into the housing. The use and construction of such mechanism is not important to the present invention and is therefore not described herein. A satisfactory abrader device has a bundle of glass fibers approximately ⅛" in aggregate diameter.

For purposes of the present invention, the fibers, although each may be relatively flimsy, may, when projected as a bundle approximately ⅛" beyond the open end of the housing 14, provide an exposed bundle which is sufficiently stiff for the practice of this invention, with the fibers supporting one another so as to resist flexing of individual fibers.

Figure 4:
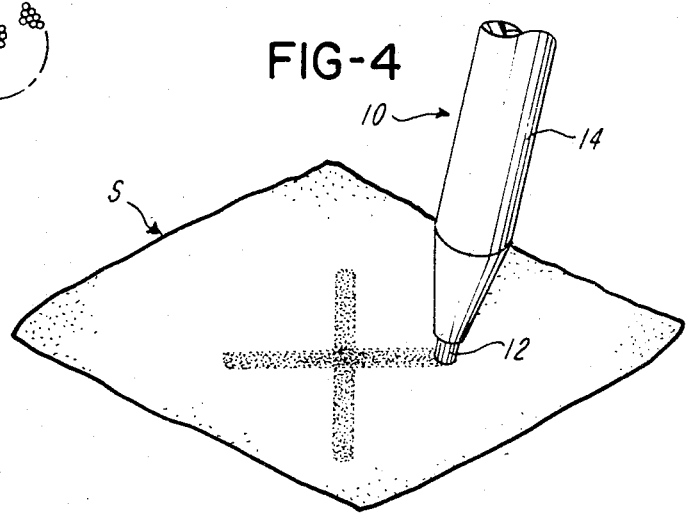
FIG. 4 is an isometric illustration of the abrader device and a patch of a patient's skin while being abraded and thereby prepared and marked by means of the present invention.

In preparing a patient for monitoring or treatment, an abrader device, such as the illustrated abrader device 10, is stroked across the skin of the patient in preferably two or more intersecting lines so as to abrade an X-shaped or star-shaped pattern which becomes readily visible on the patient's skin due to the whisking away of skin cells which comprise the outer or horny layer of epidermis. FIG. 4 thus illustrates in a schematic fashion an X-shaped marking of the skin "S" of a patient by two gently-applied strokes of a device such as illustrated in FIG. 1. As those skilled in the art will appreciate, the epidermis comprises two readily-identifiable layers. The topmost, or surface, layer is generally identified as the stratum corneum or horny layer and is comprised of cells without nuclei, and the lower layer is generally designated as the stratum germinativum and is the source of the cells which, through the process of cell aging, advance to and become the stratum corneum. It is these aging cells that have advanced into the stratum corneum that are so readily whisked away from the skin surface and, when whisked away, leave in their place a momentarily persistent whitish marking that will allow the attendant to readily identify the portion of the patient's skin that has been prepared.

By means of impedance tests wherein, after wiping the subject's skin with an alcohol pad to remove excess oil and applying prefilled electrocardiograph electrodes side-by-side to respectively unabraded skin areas and abraded skin areas, electrical signals from each electrode were compared to signals from a reference electrode applied to the patient's abdomen. It was found that a gentle skin abrasion, such as is described in this application, reduced the skin impedance variously, when several measurements taken from a single individual were averaged, as much as 69.8 percent, there being, however, a scatter of averaged impedance reduction observations from about 4.4 percent to about 69.8 percent indicating that possibly different patients or possibly different abrasion techniques provided a wide range of values reflecting the reduction of skin resistance brought about by skin preparation in accordance with the present invention.

Experience with the present invention indicates that the stratum corneum behaves as an epidermal layer which possesses a high impedance and associated therewith a high ohmic resistivity. In contrast the stratum germinativum is believed to be a relatively moist layer having a low impedance and also a low ohmic resistivity. The difference in the electrical characteristic of these two layers of the epidermis is believed traceable primarily to the amount of moisture in these layers and, thus, to the amount of ionization of the salts contained in these layers.

When an abrasion device, such as illustrated in FIG. 1, is stroked along the surface of the skin, portions of the stratum corneum or horny layer are whisked from the skin to reduce the thickness of the stratum corneum and thereby reduce the impedance of the skin surface where it will be later engaged by the electrolyte which will bridge the skin to the monitoring or treating electrode. An important observation is that the abrasion of the stratum corneum need not be accomplished over a broad area of the patient's skin. Rather it is sufficient that only a single bundle of bristles lightly abrade or scratch a small area of the stratum corneum to accomplish an adequate signal transfer between the stratum germinativum and the monitoring or treating electrode.

The tests described in this application involved prefilled electrodes, these being electrodes that were provided with an electrolyte distributed throughout an electrolyte supporting sponge or the like. As long as the electrolyte is permitted to engage even a thinly abraded area of the skin, there is an adequate signal transfer and it is ordinarily not necessary to multiply the number of scratches or abrasions and thus the aggregate skin area exposed by abrasion to obtain satisfactory results. While the tests were performed with prefilled electrodes, similar results may be obtained if the electrolyte were separately applied to the prepared skin of the patient and later contacted by the electrode.

While the device depicted in FIG. 1 is described as comprising bristles of a stiff fiber such as a glass fiber, it will be readily apparent to those skilled in the art that other fibers, such as fibers of nylon or other plastics, may be suitably employed in the present invention.

In the practice of the present invention, the abrader device illustrated in FIG. 1 is sterilized before first use by any of the known techniques for sterilization of medical equipment, the preferred mode of sterilization involving exposure of the device 10 to a sufficient intensity of X-radiation or gamma radiation for an adequate period of time.

The device when irradiated has already been packaged in a conventional container 16, such container being substantially moisture and air impervious, an example being a polyethylene bag which is used to protect the irradiated device 10 until the package is opened for first use. The device 10 is of a sufficiently economical construction that it may, at the option of the attendant, be discarded immediately after use; however, if the device is properly cleansed before any subsequent use as by immersion in alcohol, the risk of infection is ordinarily sufficiently small that one abrader may be used for the skin preparation of numerous patients. When alcohol cleaning is used, the alcohol is preferably permitted to evaporate so that the marking quality of the described instrument is not diminished by a transfer of alcohol to the skin.

Although the preferred embodiment of the present invention has been described, it will be understood that various changes may be made within the scope of the appended claims.

I claim:

1. A product comprising a substantially moisture and air impervious container and a pencil-like device packaged in said container, said pencil-like device comprising a housing and a bundle of relatively stiff fibers gathered together by and retained in the housing, said gathered fibers being stiff enough to dislodge cells from the horny layer of skin and said housing having an opening through which ends of said fibers project outwardly from said housing, said container and said device being sterilized by irradiation so that upon removal of said device from said container said device will be substantially sterilized and useful for stroking the skin of a patient in preparation for application of an electrolyte for bridging the stroked skin to a signal conductor.

2. The product of claim 1 wherein said bundle of fibers comprises fiberglass fibers.

3. The product of claim 1 wherein said fibers are sufficiently stiff to cause a whitening of the skin when they are gently stroked along the skin.

4. The product of claim 3 wherein said bundle of fibers comprises fiberglass fibers.

5. The method of preparing a subject for monitoring or treatment with an electrode, which method comprises the steps of:

gently stroking with a bundle of fibers a portion of an outer layer of the skin of the subject in a region overlying tissue to which electrical contact is to be made, said bundle of fibers being stiff enough to dislodge cells from the horny layer of skin and, in addition, being stiff enough to cause the stroked portion of skin to be marked by a change of color for moments following such stroking; and thereafter locating the marked surface of skin and applying thereto electrolyte for bridging the marked skin to a signal conductor.

6. The method of claim 5 in which the stroked portion of skin is whitened.

7. The method of preparing the skin of a patient in a region to be examined or treated, said method comprising the steps of forming a bundle of fibers, sterilizing said fibers, and stroking the skin of the patient with ends of said fibers to remove epidermal cells from such skin.

8. The method of claim 7 further including the step of storing said fibers in a protective container, said fibers being sterilized by irradiating said fibers while in said container.

9. The method of claim 8 wherein said container is a polyethylene bag.

10. The method of claim 7 including the step of confining said fibers in a housing having an opening through which ends of said fibers project.

11. The method of claim 7 wherein the fibers of said bundle, when collected into said bundle, support one another to resist flexing of said fibers when an end of said bundle is stroked across said skin.

12. The method of claim 7 wherein said fibers are glass fibers.

* * * * *